(12) United States Patent  
Drasler

(10) Patent No.: US 9,011,512 B2  
(45) Date of Patent: Apr. 21, 2015

(54) LARGE VESSEL CLOSURE DEVICE AND METHOD

(76) Inventor: William Joseph Drasler, Minnetonka, MN (US)

( * ) Notice: Subject to any disclaimer, the term of this patent is extended or adjusted under 35 U.S.C. 154(b) by 329 days.

(21) Appl. No.: 13/401,794

(22) Filed: Feb. 21, 2012

(65) Prior Publication Data

US 2012/0221089 A1 Aug. 30, 2012

Related U.S. Application Data

(60) Provisional application No. 61/463,969, filed on Feb. 25, 2011.

(51) Int. Cl.
*A61F 2/06* (2013.01)
*A61F 2/958* (2013.01)
*A61F 2/962* (2013.01)

(52) U.S. Cl.
CPC ................. *A61F 2/958* (2013.01); *A61F 2/962* (2013.01)

(58) Field of Classification Search
USPC ........................ 623/1.11, 1.12, 1.15; 606/213; 604/96.01, 915–921, 101.01–101.05, 604/102.01–102.03
See application file for complete search history.

(56) References Cited

U.S. PATENT DOCUMENTS

| | | | | |
|---|---|---|---|---|
| 5,003,989 A * | 4/1991 | Taylor et al. | | 600/585 |
| 5,195,535 A * | 3/1993 | Shank | | 600/585 |
| 5,242,394 A * | 9/1993 | Tremulis | | 604/96.01 |
| 5,383,889 A * | 1/1995 | Warner et al. | | 606/192 |
| 6,063,112 A * | 5/2000 | Sgro | | 623/1.12 |
| 6,193,706 B1 * | 2/2001 | Thorud et al. | | 604/533 |
| 6,217,526 B1 * | 4/2001 | Frassica | | 600/585 |
| 6,248,082 B1 * | 6/2001 | Jafari | | 600/585 |
| 2002/0002400 A1 * | 1/2002 | Drasler et al. | | 623/1.15 |
| 2002/0147491 A1 * | 10/2002 | Khan et al. | | 623/1.11 |
| 2007/0239257 A1 * | 10/2007 | Weber et al. | | 623/1.15 |
| 2008/0132989 A1 * | 6/2008 | Snow et al. | | 623/1.12 |

* cited by examiner

*Primary Examiner* — Katrina Stransky

(57) ABSTRACT

A low profile stent device consisting of a stent plus an optional covering is placed percutaneously into a blood vessel to provide vascular closure to a nearby large diameter arteriotomy site. A self-expanding stent device is mounted onto a balloon for postdilitation and is held in a small diameter configuration by an outer case. A balloon expandable stent device has hinge and strut features that provide it with crush resistance. The cone and sheath of the deliver catheter serves as a dilator and introducer sheath to assist in delivery. An attachable guidewire reduces profile by eliminating a guidewire lumen. A locator balloon placed through the large diameter arteriotomy introducer sheath assists positioning.

18 Claims, 12 Drawing Sheets

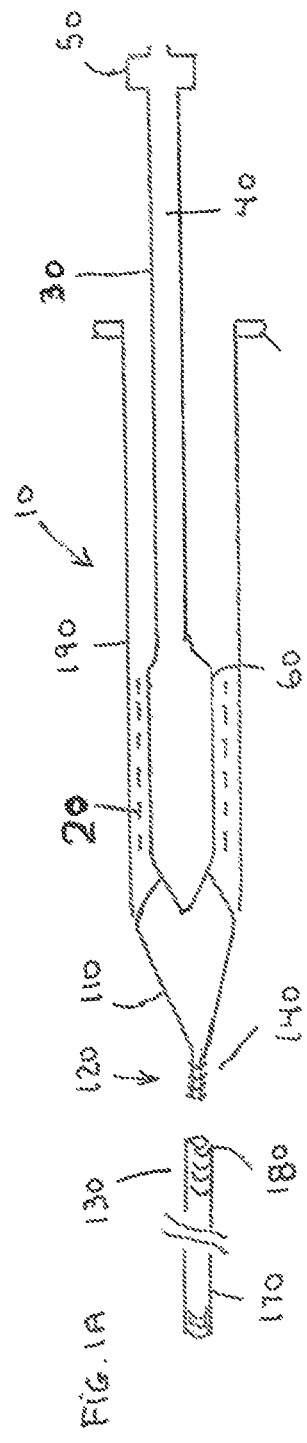

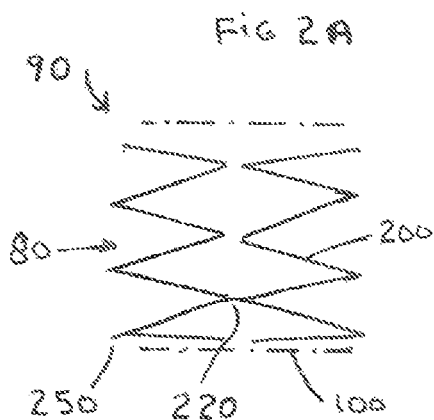
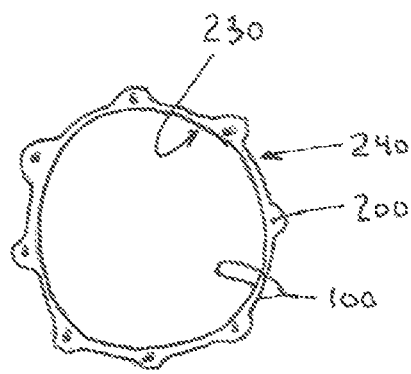
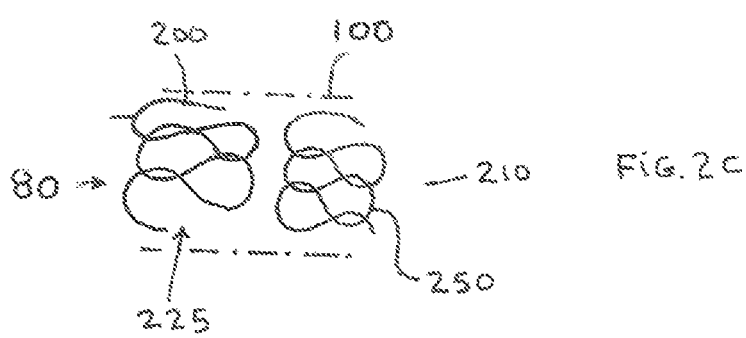
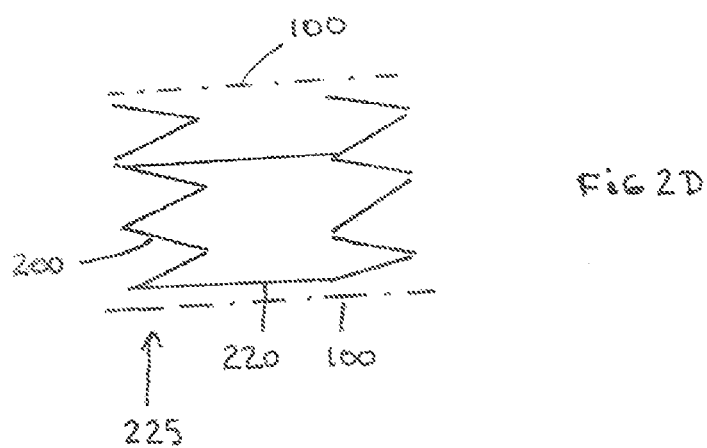

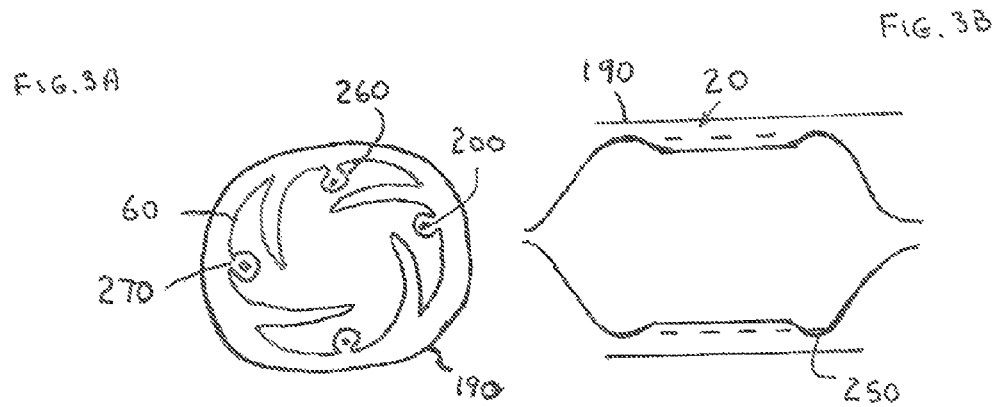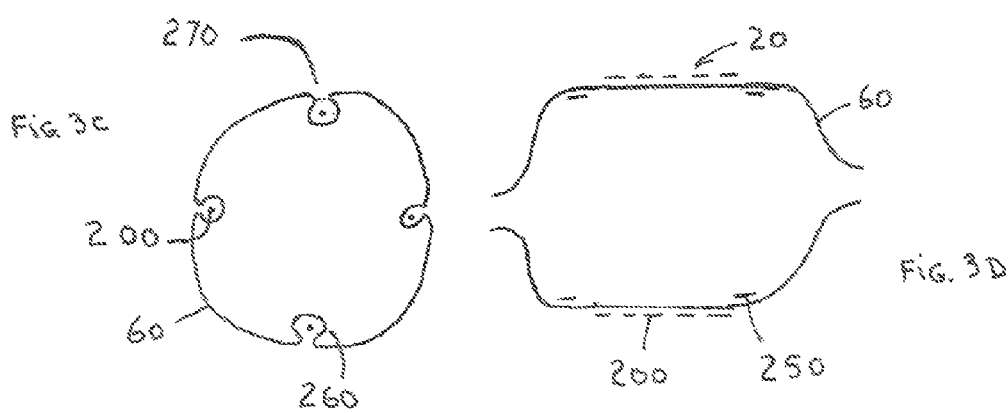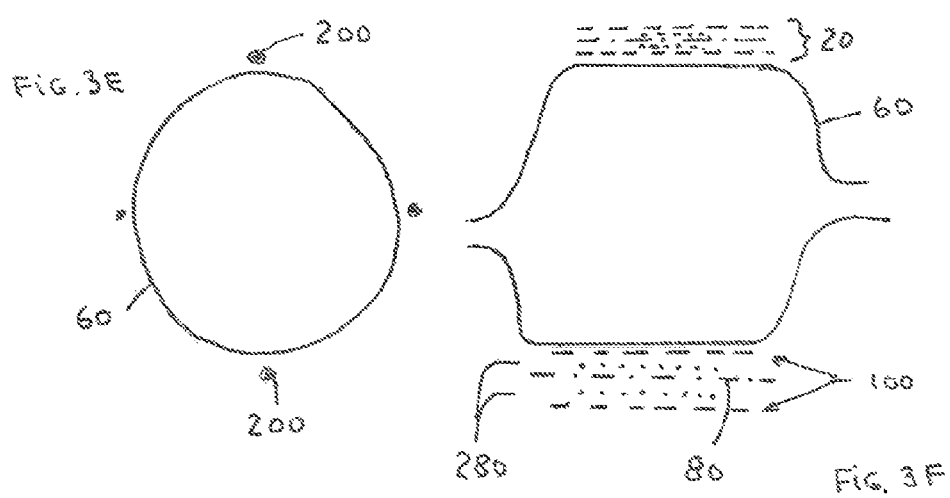

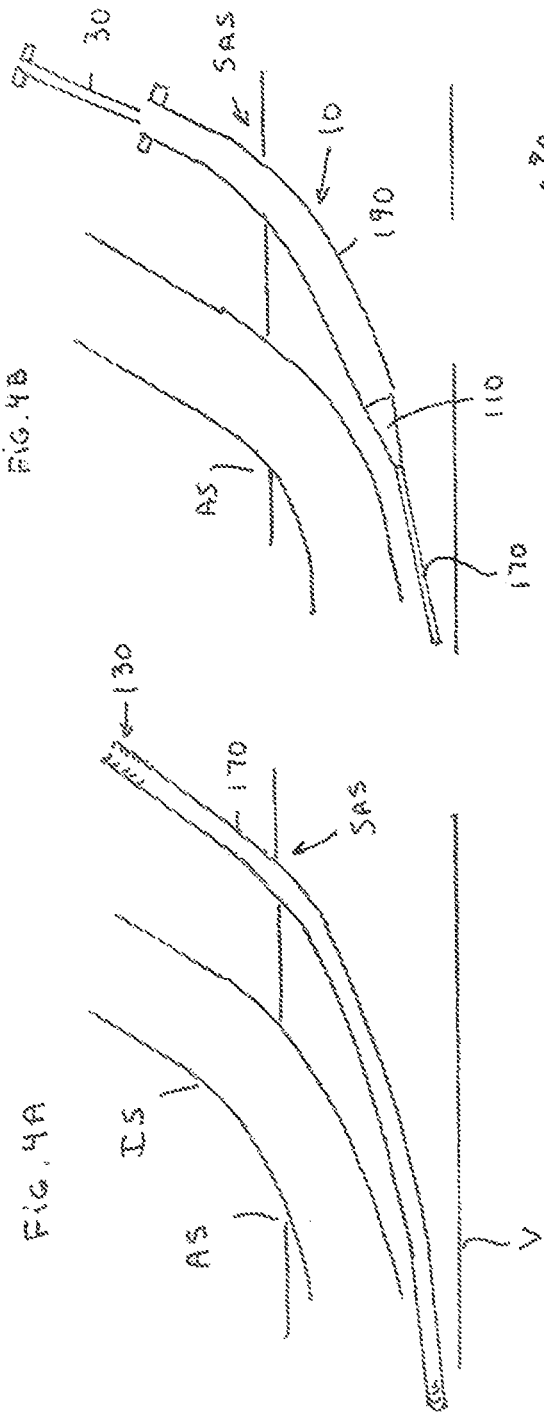

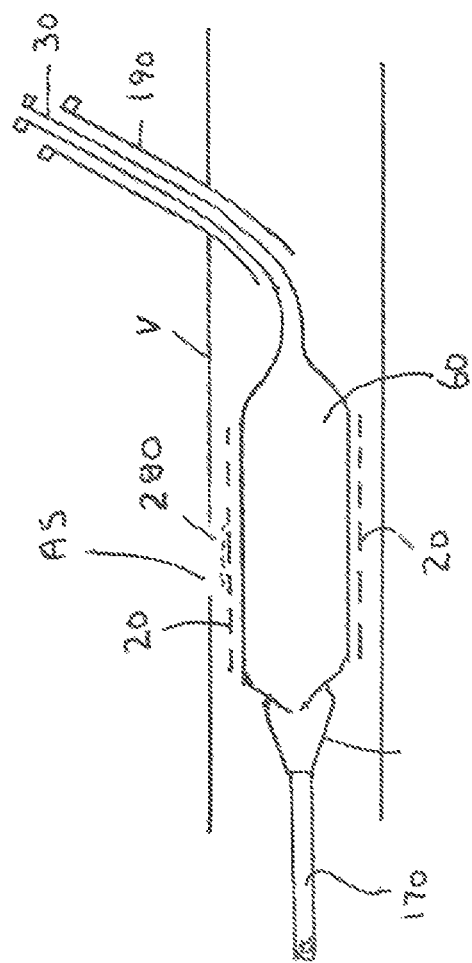
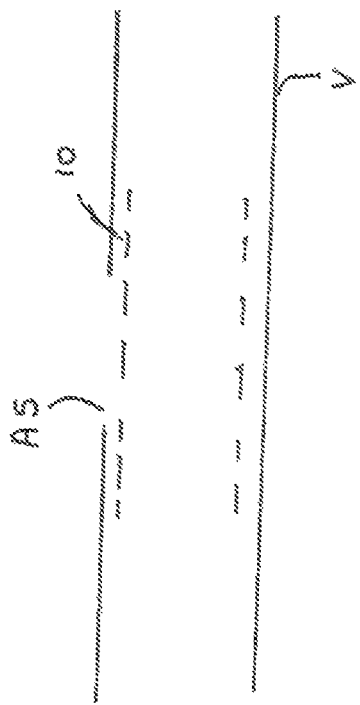

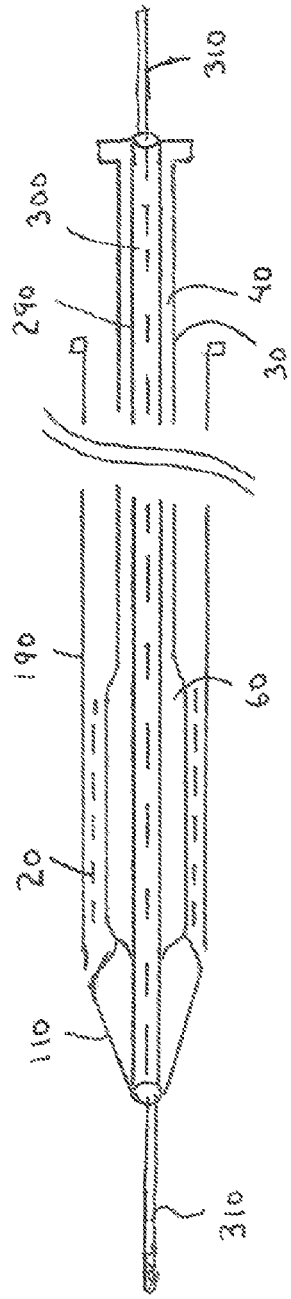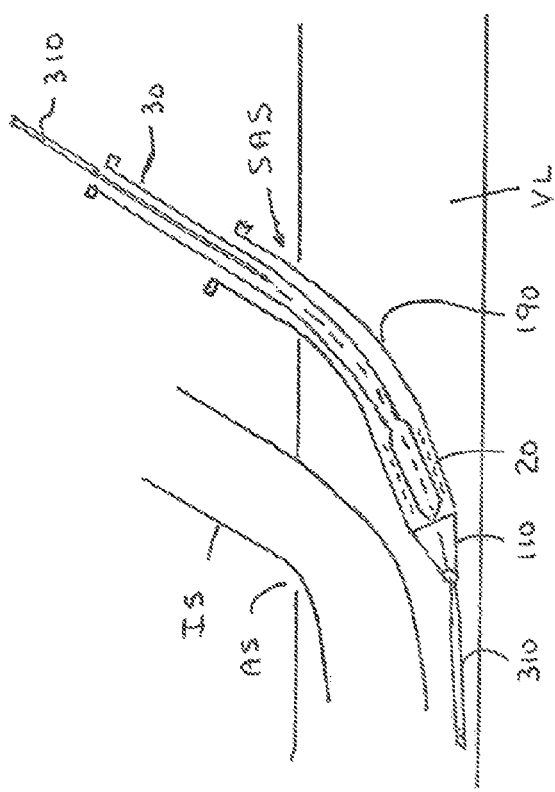

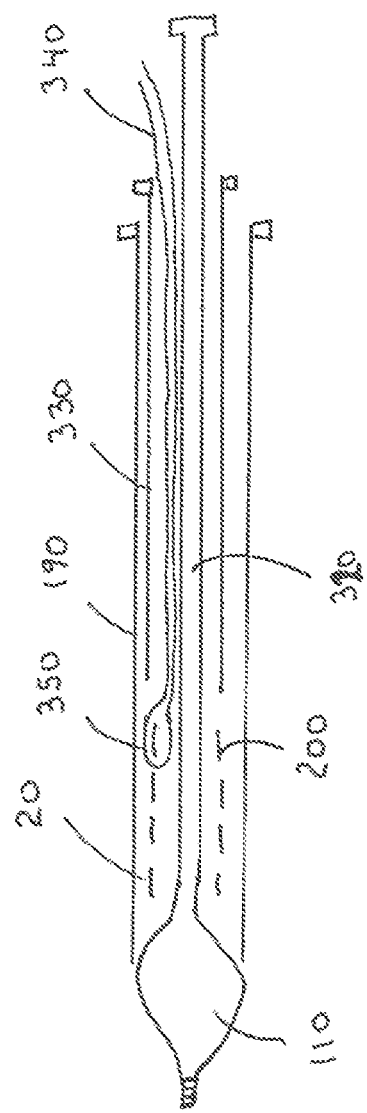

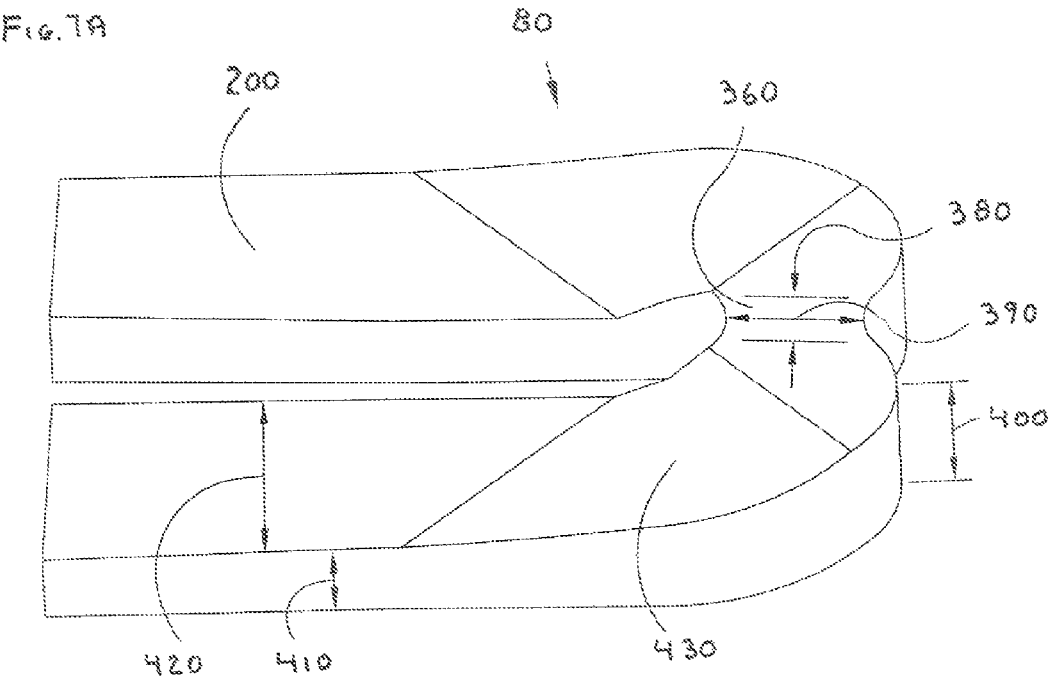

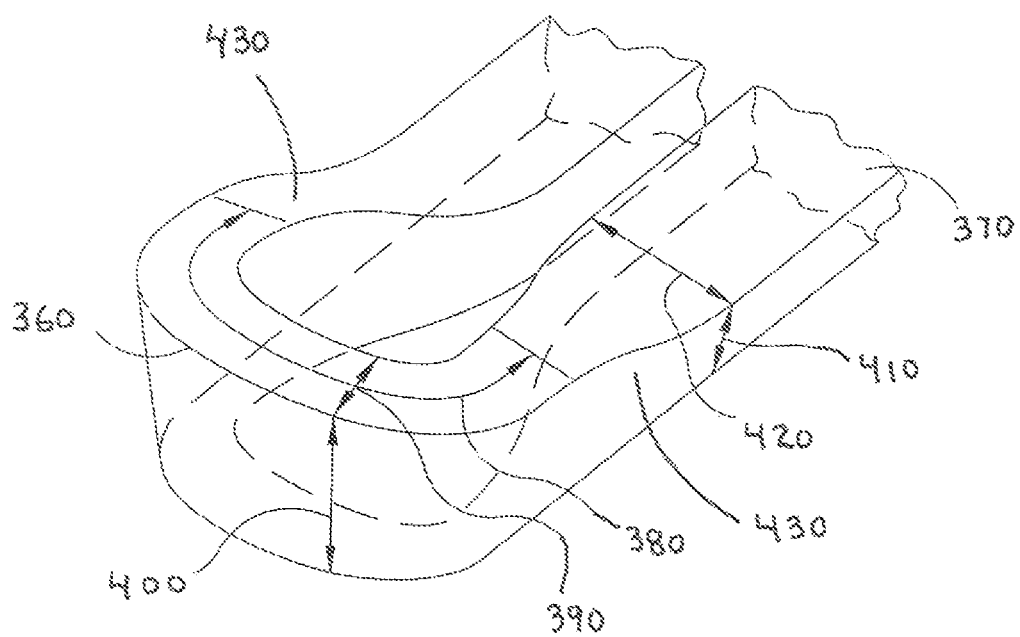

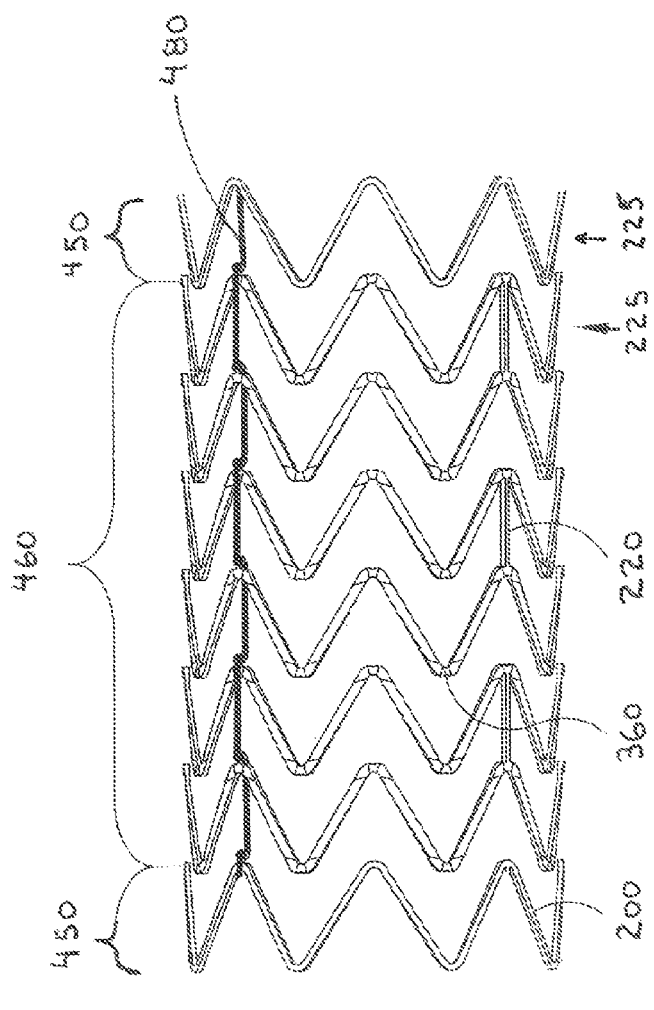
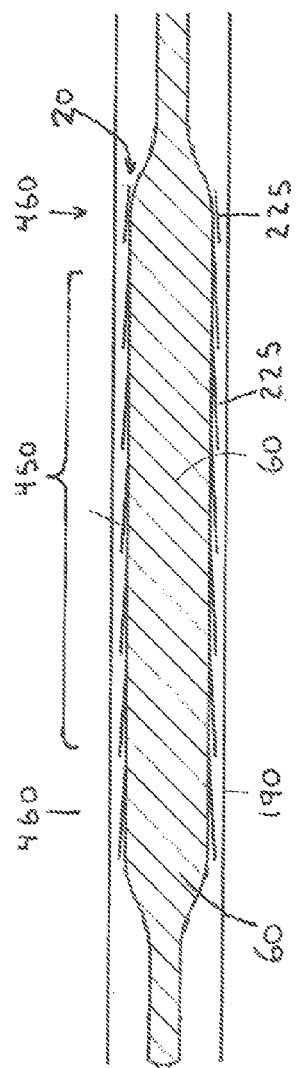
FIG. 9A
FIG. 9B

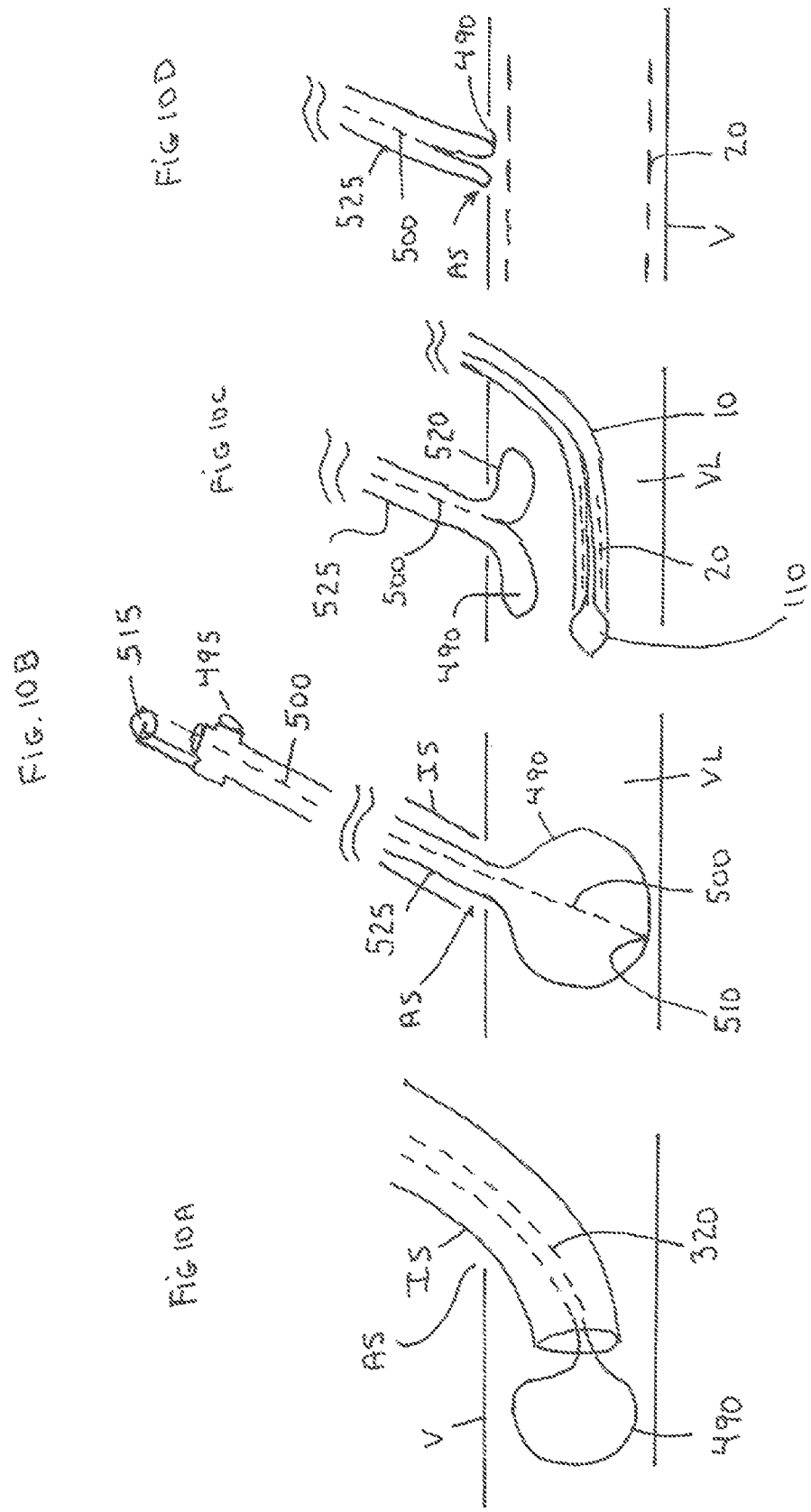

LARGE VESSEL CLOSURE DEVICE AND METHOD

CROSS REFERENCE TO RELATED APPLICATIONS

This patent application makes reference to and thereby incorporates all information found in U.S. Pat. Nos. 6,421, 763; 6,312,460; 6,475,237; 6,451,051 which describe stents and attachment means having hinges and struts. This patent application also makes reference and thereby incorporates all information found in U.S. patent application Ser. No. 12/378, 081 by Joseph M. Thielen and William J. Drasler, filed 11 Feb. 2009 entitled Peripheral Overlap Stent. This patent application makes reference to and includes all information found in the provisional patent application No. 61/463,969 entitled Large Vessel Closure Device and Method, filed 25 Feb. 2011 by William J. Drasler and Joseph M. Thielen.

FIELD OF THE INVENTION

This invention relates to an interventional catheter that is placed into a lumen of the body to deliver a stent device to an artery, vein, or other tubular member of the body in a smaller diameter configuration and allows it to expand to a larger diameter configuration. Additionally, the invention relates to providing a very low profile catheter that is able to percutaneously deliver a covered stent to the body vessel to cover or close an opening in the wall of the vessel.

BACKGROUND OF THE INVENTION

Delivery of stents or covered stents to the vasculature is often provided via percutaneous delivery that involves the Seldinger approach. Following access to the vasculature via a needle, a guidewire is entered through the needle and the needle is removed. With the guidewire in place in the vessel, a dilator with an external introducer sheath is then advanced over the wire into the vessel. Upon removal of the dilator, the introducer sheath is left in place to provide an access channel for entry of an interventional catheter. This introducer sheath enlarges the vessel to a diameter that is larger than the interventional catheter, and makes the diameter of the access site larger than necessary in some cases. Closure of the access site can then present a problem for large diameter access sites that are intended for large diameter interventional catheters, particularly when the patient is being heparinized.

Transcatheter Aortic Valve Implantation (TAVI), Abdominal Aortic Aneurysm repair, and other minimally invasive procedures require that large introducer sheaths be placed percutaneously into the vasculature in order to provide passage for these devices intended to repair or replace the damaged vessel or body tissue. Often the catheters have profiles that range from 16 to 21 French or larger. Vascular closure of such large arteriotomy sites following the removal of the large introducer sheath can be very difficult and often can require surgical intervention. Most percutaneous closure device do not perform well to close such large arteriotomy sites where the diameter of the arteriotomy is almost as large as the diameter of the vessel. One closure device that utilizes an anchor material on the inside of the vessel attached to a plug material on the outside works well for smaller diameter access closure but is not reliable for larger diameter access site closure. Other percutaneous closure devices that utilize sutures also have difficulty ensuring that the large diameter arteriotomy site is consistently closed. Manual compression of the large diameter access site can require a long period of time and can be associated with continued blood oozing and the formation of a hematoma.

What is needed is a device that can easily and consistently close a large diameter access site. The device should allow closure of the access site within only a few seconds after removal of the large introducer that provided access to the large interventional catheter. Since the femoral access site often contains plaque deposit, the closure device should not be limited by such plaque. Also, since the femoral artery is generally the access site of preference, the device should not be prone to kinking or collapse due to external pressure that may be applied to the skin or due to bending that can occur at the femoral arterial access site. The profile of a vascular closure device should have a profile that allows its use without requiring excessive or complicated delivery.

SUMMARY

The present invention is well suited to use as a closure device for closure of an access site following a TAVI procedure or other percutaneous procedure that requires a large interventional catheter wherein the access site is not easily sealed using standard manual compression via thumb pressure or the current percutaneous closure devices. The present invention can also be used to percutaneously deliver a stent or a covered stent to the lumen of a vessel for any purpose such as enlarging a stenotic region of the vessel or repairing a dissected or injured vessel using a very low profile delivery catheter.

The delivery catheter of the present invention is a very low profile catheter that is able to deliver a self-expanding or balloon expandable stent device to the interior of a vessel. An external sheath or case holds the self-expanding stent device into a small diameter configuration on the outside of a balloon that has a very low profile. A molded plastic tapered cone at the distal end of the balloon serves as a dilator. The external sheath or case serves as an introducer sheath to hold the second smaller arteriotomy site outwards. The distal tip end of the cone is configured to be attached to the proximal end of a guidewire configured to receive it. A special guidewire of the present invention can be introduced into the vessel and can subsequently be attached to the catheter cone for introduction directly into the vessel. The low profile of the device potentially obviates the need for a vascular closure device to close the opening created by the delivery device of this invention.

Although the present delivery device is intended primarily for closing a large opening in an artery using a self-expanding stent device that has a covering, it is understood that the invention can also be used to deliver a self-expanding stent without a covering. Also, a balloon expanding stent can be used with the present invention instead of a self-expanding stent device. For sealing an access site in the femoral artery, a self-expanding stent device offers the advantage that it will not crush by exposure to external forces and it is able to flex from exposure to external forces. A balloon expandable stent offers the advantage of compressing any luminal plaque and thereby providing tight apposition of the stent device against the vessel wall to form a tight seal without leakage.

In one embodiment of the delivery catheter a low profile balloon at the distal end has a covered self-expanding stent positioned around the deflated balloon. The balloon membrane is wrapped around a portion of the stent struts to hold the stent adjacent to the balloon and prevent it from embolizing or moving axially until desired. The covering on the self-expanding stent can be a thin-walled (less than 0.001 inch wall) expanded polytetrafluoroethylene (ePTFE) membrane, a thin fibrous polyurethane, or other thin porous membrane of similar thickness. The covered stent is held into a small diameter configuration by an external sheath or case that can move proximally to expose the stent for delivery.

Bonded to the distal end of the balloon is a nondeformable plastic tip or cone with a gradual taper that is similar to a taper found on a dilator catheter; the taper on one side of the cone can be approximately 15-25 degrees off of the axis. A gradual taper will allow the cone to easily dilate or "Dotter" the arteriotomy site as it is advanced into the vessel. At the distal end of the cone is located an attachment feature or element that allows the cone to become attached without unwanted release to a receiving element that is located on a special guidewire that is an element of the present invention.

In one embodiment for the method of use of the present invention, a standard introducer sheath of approximately 16-21 French size has been previously inserted into the femoral artery or other blood vessel and is directed towards the aorta for use in delivery of a TAVI catheter or other large catheter. For the method of use for the present invention the standard Seldinger approach is used to gain access to the femoral artery at a location just distal (approximately 1 to 3 cm) to the large TAVI access site and a needle access is directed into the vessel in a direction toward the large diameter TAVI introducer sheath. A guidewire of the present invention ranging in diameter from 0.010 to 0.038 inches is introduced into the needle and advanced into the vessel and the needle is removed. The guidewire has a receiving element located at its proximal end. The attachment element at the distal end of the cone is attached to the receiving element of the guidewire. The attachment of the guidewire to the cone can be accomplished via a swaging step or by forming an interlocking coupling. The delivery catheter which includes the guidewire are together advanced through the arteriotomy site and into the vessel. The cone dilates the arteriotomy site as the catheter is advanced into the vessel and the external sheath or case holds the arteriotomy site outwards as the delivery catheter is advanced further into the vessel. The delivery catheter is advanced until the cone comes into contact with the large TAVI introducer sheath. The cone and case of the delivery catheter of the present invention obviate the need for a separate dilator and introducer sheath and thereby reduces the size of arteriotomy access site.

Upon removal of the larger diameter TAVI introducer sheath, the delivery catheter is advanced a prescribed distance to position the stent device across the large diameter arteriotomy site. The case is retracted proximally to expose the stent device and the balloon is inflated to place the stent device into contact with the arteriotomy and close the access site. As the balloon is inflated the wrap attachments of the balloon with the struts of the self-expanding stent device will unwrap and allow the stent to be released into contact with the vessel wall. The balloon inflation ensures that the stent device is placed into intimate contact with the vessel wall and ensure that any plaque deposits on the vessel wall are dilated, crushed, or covered. After delivery of the covered stent device, the delivery catheter is removed from the vessel.

The delivery catheter of the present invention is intended to deliver a self-expanding stent device that can extend up to 10 mm with its external sheath or case having a diameter of approximately 4-5 French (F). At this low profile it is not expected that this additional access site for delivery of the present invention will require a closure device and is expected to close with minimal or no manual compression requirement. The low profile of the present device is attained in part by having none or minimal internal structures in the balloon. Furthermore, there is no additional dilator or introducer sheath for the present delivery catheter invention to pass through. The cone and the case of the present invention act as the dilator and the low profile introducer sheath. The separate guidewire element of the invention allows the guidewire to be placed via the standard Seldinger approach, but the subsequent guidewire attachment to the cone obviates the need for the standard dilator and introducer sheath. The delivery catheter which includes the guidewire can be accessed directly into the vessel with direct contact of the cone and case with the low profile arteriotomy site, and advanced easily for short distances as a fixed wire catheter. The short distance from the access site for the present invention to the location of the deployment of the stent device is very short, 2-10 cm, and less than 4 cm in most cases. For these cases where the delivery catheter of the present invention is used to provide closure to a large arteriotomy site, the entire catheter can be very short in length ranging from approximately 6 to 20 inches long.

One element of the present embodiment of the present invention is the stent device. The stent device can be a stent such as a balloon expandable stent or a self-expanding stent; alternately, the stent device can have a cover attached to it. In one embodiment of the stent device, a Nitinol stent is formed into a zigzag pattern although any stent pattern can be used with the present invention. A cover formed of ePTFE can be located on the outside and inside surface (230) of the stent and bonded together. Various configurations of the stent zigzag pattern can be used and a variety of linkage or connection patterns can be used to attach one zigzag ring to a neighboring ring to form a generally cylindrically shaped stent. Alternately, a small length ringlet can be placed at each end of the stent device with a covering extending in between. The stent and its covering can be formed from biodegradable polymers or metals, the covering can be a biodegradable tissue material obtained from an animal source or formed from processed collagen or other tissue materials. The cover for the stent can extend throughout the entire length of the stent or it can occupy only a central portion of the stent.

As the external sheath or case is retracted it can be important to hold onto the self-expanding sent device such that it does not jump axially or embolize uncontrolled into the artery. To address this issue, the present invention provides an option of a temporary attachment of the balloon with the struts of the stent device. The balloon can be wrapped around a portion of some struts of the stent. As the balloon wraps around the struts, the stent can be temporarily held to the balloon such that as the balloon is inflated the balloon is required to let go of the stent device. By providing the wrap attachments, the stent device can be delivered accurately to the desired site.

In an alternate embodiment of the present invention a small guidewire lumen extends throughout the length of the delivery catheter and out of distal cone. The ID of the guidewire lumen (300) can range from 0.010 to 0.040 inches. Following Seldinger approach to obtain access to the vessel, a guidewire can be placed into the vessel. The delivery catheter of this embodiment can then be used to follow over a standard guidewire and enter the vessel. The device and method of use is thereafter similar to that described for the last embodiment; the profile is not quite as favorable due to the presence of the internal guidewire tube.

It is understood that the device of the present invention is not limited to vascular closure and is not limited to only its use as a low profile delivery catheter. When used for large diameter stent device delivery, the dimensions of delivery catheter elements can be altered proportionally and accordingly. Also, the use of the present invention for delivery of balloon expanding stents or stent devices can also accomplish many of the benefits described for the self-expanding stent device.

In yet another embodiment a self-expanding stent either with or without a covering can be located within the external sheath or case of the delivery catheter without positioning it onto a balloon of a balloon catheter. A pusher tube placed over the catheter shaft can ensure that the stent device is pushed out of the case as the case is being withdrawn. A control fiber attached to the stent device ensures that the self-expanding stent is not allowed to embolize within the blood vessel. A post dilation of the self-expanding stent device may be necessary to ensure that it is fully engaged with the vessel wall to prevent blood leakage through the arteriotomy site. The pusher tube and the control fiber can be used with the embodiments that contain a balloon catheter.

In a further embodiment the stent or the stent used in the stent device can be a hinge stent similar to the balloon expandable hinge stent described in the patents and patent application cross referenced in this patent application. The balloon expandable hinge stent has hinge and strut features that allow the stent to be expanded by a balloon but is not susceptible to forming a permanently crushed shape due to exposure to external forces or forces imposed by muscle groups. The hinge stent design can be securely mounted and delivered on a deflated balloon at the distal end of a balloon catheter. The balloon expandable stent or stent device is not able to embolize upon release of the external sheath or case due to its tight crimped fit over the balloon.

In yet a further embodiment the stent or stent device can be a self-expanding hinge stent as described in the US patents and US application cross referenced in this application. The material of construction for a self-expanding stent can be the same as that used for standard self-expanding stents used in the industry. Alternately, it can be made using stainless steel and rely on dimensions of the hinges and struts to provide it with the self-expanding characteristics. A stent or stent device formed with the hinge structure described can have one portion of the stent that is self-expanding and another portion that is balloon expandable; both portions can be formed from the same material; the balloon expandable portion can assist in holding the stent device onto a balloon of a balloon delivery catheter.

In yet another embodiment a locator balloon is placed through the large diameter introducer sheath used to deliver the TAVI device. The locator balloon can serve to locate the position of the delivery catheter such that it is positioned directly adjacent to the large diameter arteriotomy site prior to release of the stent device. The locator balloon can have a tether located on its inner surface that allows the balloon to be inwardly folded such that passage of the delivery catheter can be accomplished without risk of bleeding or hematoma until the stent device has been significantly or fully deployed at the arteriotomy site.

Another embodiment provides an implantable locator balloon. The locator balloon provides a positioning benefit for the delivery catheter and holds the arteriotomy site from leakage. As the stent device is released and expanded into place via either a balloon expandable version or a self-expanding version, the locator balloon is pushed into the arteriotomy site and serves as a plug material to ensure that the arteriotomy site will not encounter blood leakage.

BRIEF DESCRIPTION OF THE DRAWINGS

FIG. 1A is a plan view of the delivery catheter with the guidewire unattached.

FIG. 1B is a plan view of the delivery catheter with the guidewire attached via a threaded joint.

FIG. 1C is a plan view of the delivery catheter with the guidewire attached via a swage joint.

FIG. 2A is a longitudinal plan view of the stent device with the stent and covering.

FIG. 2B is a transverse plan view of the stent device with the stent and covering.

FIG. 2C is a longitudinal plan view of the stent device with the stent and covering with individual ringlets and overlapping of struts in a circumferential direction.

FIG. 2D is a longitudinal plan view of the stent device with the stent and covering with ringlets that are connected.

FIG. 3A is a transverse plan view of the balloon with wrap attachments to the stent and located within the case.

FIG. 3B is a longitudinal plan view of the balloon with wrap attachments to the stent and located within the case.

FIG. 3C is a transverse plan view of the balloon with wrap attachments to the stent and a balloon bond.

FIG. 3D is a longitudinal plan view of the balloon with wrap attachments to the stent around an end strut.

FIG. 3E is a transverse plan view of the fully inflated balloon showing release of the stent device.

FIG. 3F is a longitudinal plan view of the fully inflated balloon showing the released stent device having two covering layers and blood coagulant material.

FIG. 4A is a plan view of the guidewire introduced into the blood vessel a small distance distal to the arteriotomy site with the large introducer sheath.

FIG. 4B is a plan view of the delivery catheter advancing into contact with the large introducer sheath.

FIG. 4C is a plan view of the delivery catheter positioned in the blood vessel with the stent device adjacent to arteriotomy site.

FIG. 4D is a plan view showing the case being withdrawn and exposing the stent device to the arteriotomy site.

FIG. 4E is a plan view of the stent device being expanded into apposition with the blood vessel via a dilatation balloon.

FIG. 4F is a plan view showing the stent device creating hemostasis at the arteriotomy site.

FIG. 5A is a plan view of another embodiment of the delivery catheter having a guidewire tube and providing passage for a standard guidewire.

FIG. 5B is a plan view showing advancement of the delivery catheter over a standard guidewire into contact with a large introducer sheath.

FIG. 6 is a plan view of a delivery catheter without a balloon and having a control fiber to hold the stent device.

FIG. 7A is a perspective view of one embodiment for a hinge and strut geometry for a balloon expandable stent having with one hinge with a short hinge length joining two struts to be used in the stent device.

FIG. 7B is a perspective view of one embodiment for a hinge and strut geometry for a balloon expandable stent having with two hinges each with short hinge lengths joined to a node and joining two struts to be used in the stent device.

FIG. 8 is a perspective view of one embodiment for a hinge and strut geometry for a self-expanding stent having a long hinge length to be used in the stent device.

FIG. 9A is a perspective view of the stent used in the stent device having one portion that is balloon expandable located in the central region of the stent and self-expanding portions located at each end of the stent.

FIG. 9B is a plan view of the stent used in the stent device having one portion that is self-expanding located in the central region of the stent and balloon expandable portions located at each end of the stent.

FIG. 10A is a plan view of the locator balloon advanced through the introducer sheath and positioned in the blood vessel.

FIG. 10B is a plan view of the locator balloon inflated to fill the blood vessel lumen.

FIG. 10C is a plan view of the locator balloon forming inner folds from traction place on a tether fiber thereby allowing for passage of the delivery catheter into position adjacent the arteriotomy site.

FIG. 10D is a plan view of the locator balloon being fully retracted into the locator balloon shaft and the stent device being placed into apposition with the wall of the blood vessel.

DETAILED DESCRIPTION OF THE INVENTION

Figure 11A:
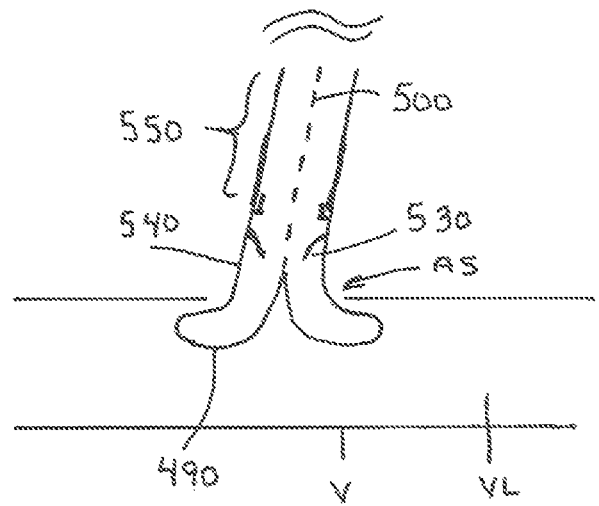
FIG. 11A is a plan view of an implantable locator balloon located within the arteriotomy site.

The present invention as shown in FIGS. 1A-1C is a delivery catheter (10) for delivering a stent device (20) percutaneously to a vessel lumen. The use of this invention can be for delivering a stent device (20) following angioplasty or during the angioplasty procedure. The stent device (20) can be a drug eluting stent such as a balloon expandable stent or a self-expanding stent or it can be a stent graft or covered stent. One of the more advantageous applications for the delivery catheter (10) of the present invention is for the closure of a large arteriotomy site such as one made in the femoral artery for delivery of a large catheter such as a TAVI device or an AAA device. Since the standard introducer sheath used in these procedures are approximately the same size as the vessel diameter, i.e., 16-21 French, the normal vascular closure devices and methods do not work well. The present delivery catheter (10) is intended to gain access in the same femoral artery or other artery that is typically entered for the TAVI procedure only at a new access site that is just a small distance distal to the TAVI access site. Since the present invention has a very small profile, providing this new second access site does not create a significant drawback and provides a definite device and method for sealing the large TAVI access opening easily, quickly, and consistently which currently is a source of vascular complications using existing sealing devices and methods.

An embodiment of the delivery catheter (10) is shown in FIGS. 1A-2B. A balloon tube or shaft (30) with a balloon inflation lumen (40) extends from the balloon manifold (50) through the delivery catheter (10) to the balloon (60). The distal end of the balloon (60) is closed by thermal methods, adhesive, solvent, bonding a plastic filler or other method. The balloon (60) can be formed from polyethylene terephthalate, polyethylene, or any material commonly used for making an angioplasty balloon. It is anticipated but not required that the same tubing that is use to form the balloon (60) can be used for the balloon tube or shaft (30).

On the outside of the balloon (60) is mounted a stent device (20); the stent device (20) can be a stent (80) or a covered stent (90). In the preferred embodiment for providing a vascular closure device the stent device (20) can be a self-expanding stent that has a covering (100); alternately the stent (80) can be either balloon expandable or self-expanding and it does not require a covering (100). The distal end of the balloon (60) is bonded to a conical dilator or cone (110) that is formed from a hard plastic, or metal, or other nondeformable material that is generally lubricious and can serve as a dilator. Materials for the cone (110) include polyethylene, delrin, fluorinated polymers, and other plastics, composites, or metals. At the distal end of the cone (110) is an attachment feature or attachment element (120). The attachment element (120) can be a stud that has a locking feature, a plastic or metal stud that has a lock snap that springs shut on a receiving element (130), a threaded stud (140) (as shown in FIG. 1A) that can be used to form a threaded joint (150) as shown in FIG. 1B, a metal stud that can receive a mating cylinder that can be swaged upon to form a swage joint (160) as shown in FIG. 1C, or an indented receptacle that has a non-slip material on its surface, a threaded receptacle (180), or other locking receptacle.

Another element of the invention is a guidewire (170) having a receiving element (130) that is able to be attached to the attachment element (120) at the distal end of the cone (110). The receiving element (130) of the guidewire (170) can be a stud, a threaded joint (150), a threaded receptacle (180) as shown in FIGS. 1A and 1B and can be used to form a threaded joint (150) as shown in FIG. 1B, a snapping feature that mates with the attachment element (120) of the cone (110) or other mating member that allows the guidewire (170) to be readily but securely joined to the cone (110) of the delivery catheter (10).

Providing the guidewire (170) as a separate but connectable element allows the guidewire (170) to be advanced into the vessel through an initial needle puncture and allows removal of the needle; this obviates the need for a separate dilator and introducer sheath. The guidewire (170) can range in diameter from 0.014-0.038 inch diameter and can have a length ranging from 3 cm to 40 cm. Once the guidewire (170) is attached to the cone (110), the delivery catheter (10), which includes the guidewire (170), can then be advanced together to the site of interest in the vessel.

The delivery catheter (10) of the invention has a movable external sheath or case (190) that extends over the stent device (20) and holds the stent device (20) down onto the balloon (60). The case (190) comes into contact with the cone (110) to form a smooth surface such that the combination of the cone (110) and the case (190) act in a manner similar to a standard dilator and introducer sheath. Thus with the guidewire (170) attached to the cone (110), the delivery catheter (10) can be advanced through an arteriotomy site by holding onto the case (190) and advancing the delivery catheter (10) distally. When the case (190) is retracted in a proximal direction toward the balloon manifold (50) as shown in FIG. 1B, the stent device (20) is exposed to the vessel wall. In the case of a self-expanding stent device (20), the stent device (20) can be deployed immediately upon retraction of the case (190). The stent device (20) can then be post dilated by inflating the balloon (60) as shown in FIG. 1C to ensure definite contact of the stent device (20) and the vessel wall. The present invention provides that a self-expanding stent device (20) can remain attached to the balloon (60) even after retraction of the case (190) as shown in FIG. 1B; this feature will be described further in FIGS. 2A-2D. In the femoral artery and many regions of the leg and the carotid arteries of the neck, a self-expanding stent device (20) is preferred to reduce the chances for crush deformation of the stent device (20) due to external forces applied to the stent device (20) through the skin or from muscle groups. For the case where external crush is not a significant detriment, such as for coronary stenting, a balloon expandable stent device (20) can be used; the balloon expandable stent device (20) is mounted onto the balloon (60) and is deployed upon inflation of the balloon (60). The case (190) can be used for the balloon expandable stent (80) or stent device (20) but is not required if a standard introduce sheath is used to provide entry for the stent device (20)

mounted on a standard balloon dilation catheter such as used in the medical device industry.

The stent device (20) of the present invention can include any stent (80) or covered stent (90) that is currently found in the industry. The stent (80), for example, can be formed of zigzag rings or a zigzag spiral, or it can be formed from any open or close cell patterns used in stent design, some of which are shown in FIGS. 2A-2D. The stent struts (200) can have overlapped struts (210) to help gain a lower profile as shown in FIG. 2C. The connectors (220) or links of various patterns can connect individual ringlets (225) to provide a stent device (20) with multiple connected ringlets. Ringlets (225) can overlap neighboring ringlets (225) as described in the cross-referenced patent application. The self-expanding stent (80) can be formed from Nitinol, elgiloy, or other elastic metals, composites, biodegradable materials, or elastomeric plastics. The balloon expandable stent (80) can be formed from stainless steel, Cobalt-Chrome, or other materials commonly used for stents including biodegradable materials. Biodegradable polymeric materials or biodegradable metals can be used for the stent (80) or stent device (20) construction; such materials include polyglycolic acid, polylactic acid, polyethylene glycol, tissue or collagen materials, magnesium, or other biodegradable materials used in the medical device industry.

The stent device (20) can have a thin covering (100) placed on the inside surface (230), outside surface (240) or both. One embodiment as shown in FIG. 2B has an ePTFE cover with a thickness of approximately 0.0005 inches placed on both the outside and inside surface (230)s of the stent struts (200) and bonded together around the stent struts (200) to hold it in place. The ePTFE covering (100) or other fibrous covering (100) such as polypropylene, polyurethane, or other fibrous or porous polymeric structure is porous to allow cellular penetration to enhance tissue healing but not allow significant bleeding to occur through the cover. Alternately, a tissue covering (100) such as a porcine pericardium or other biodegradable material can be used, including collagen, fibrin, or other tissue materials. The pore size for a polymeric covering should range between 2-30 microns, but this pore size is dependent upon the wall thickness.

The coverering (100) can extend along the entire surface of the stent (80) or it can cover only a portion of the stent (80) leaving the strut end (250) uncovered by the ePTFE or other cover material. Allowing the strut end (250) to remain uncovered allows the stent device (20) to be attached to the balloon (60) as shown in FIGS. 3A-3D. The stent ringlets (225) can be located, for example, at each end of the covering (100) leaving the central portion of the covering (100) without support from a stent (80), thereby having the flexibility that is desired and having the ability to be punctured again at a later time for vascular access.

The balloon (60) of the present invention is shown in a nondeployed configuration in FIGS. 3A and 3B. The balloon (60) can be wrapped around a portion of the stent strut (200) such as a strut end (250) to form a wrap attachment (260) as shown in FIGS. 3A-3D. This wrapping feature is not required by the present invention but provides a potential benefit for holding the self-expanding stent device (20) in position with respect to the balloon (60) such that the stent device (20) cannot embolize or become displaced in the vessel. In FIG. 3A a portion of the balloon (60) is wrapped around a stent strut. As the balloon (60) wraps around the strut, it can form a balloon bond (270) to another portion of the balloon (60) and form a wrap attachment (260). When the balloon (60) becomes partially inflated as shown in FIGS. 3C and 3D, the stent device (20) is still attached to the balloon (60). Further inflation of the balloon (60) as shown in FIGS. 3E and 3F causes the stent device (20) to become released from the balloon (60) as the balloon wrap attachments (260) are forced to let go of the strut ends (250). For the case where the stent device (20) is a covered stent (90), the strut ends (250) are held by the wrap attachments (260) and are released as shown in FIG. 3F. A small amount of thrombin, blood coagulant, or clotting agent (280) can be placed on the outside of the covering (100) or between the layers of the cover as shown in FIG. 3F if desired to assist in forming a clot when the stent device (20) is a covered stent (90) use to provide vascular closure.

The method of use of the delivery catheter (10) for vascular closure is shown in FIGS. 4A-4F. The method for delivery of a stent (80) or covered stent (90) to the vasculature for a different purpose is identical to this except that the site of delivery for the stent device (20) may not be for the closure of a large diameter arteriotomy site from a large catheter.

Access is made with a needle to the femoral artery at a site approximately 1-10 cm (preferably 1-3 cm) distal to a large introducer sheath, IS, being used for passage of a large diameter interventional catheter such as a TAVI or AAA catheter. The small diameter access site, SAS, for the delivery catheter (10) of the present invention could be greater than 3 cm from the large introducer for the large interventional catheter without deviating from the present invention. A guidewire (170) of the present invention having a receiving element (130) at its proximal end is advanced through the needle and past the site of the large diameter introducer sheath, IS, as shown in FIG. 4A. The needle is removed and the receiving element (130) of the guidewire (170) is firmly attached to the attachment element (120) at the distal end of the cone (110) of the delivery catheter (10). This attachment can be via screwing, swaging, via a snap fit, a one-way joint, or other joint. The cone (110) acts as a dilator to enter the arteriotomy and the case (190) acts as an introducer to hold the arteriotomy site outwards. The delivery catheter (10) is advanced along with the guidewire (170) into the vessel until the cone (110) comes into contact with the large diameter introducer. The large diameter introducer sheath, IS, can then be removed and the delivery catheter (10) is advanced a small prescribed distance if necessary to place the stent device (20) adjacent to the arteriotomy site as shown in FIG. 4C. The case (190) is then retracted in a proximal direction as shown in FIG. 4D thereby exposing the stent device (20) to the vessel, V, and the balloon (60) is inflated to press the self-expanding stent device (20) up against the vessel wall thereby covering the arteriotomy site as shown in FIG. 4E. The covering (100) on the stent device (20) covers the opening causing the blood leakage out of the arteriotomy site to cease. A small amount of thrombin or other clotting agent placed on the surface of the covering (100) or between layers of the ePTFE covering (100) can help to ensure that the blood clots quickly and leakage is maintained at a minimum. The balloon (60) is deflated and the delivery catheter (10) is then removed as shown in FIG. 4F.

In an alternate embodiment, a guidewire tube (290) with a separate guidewire lumen (300) can be placed through the balloon tube (30), the balloon (60), and through the cone (110) as shown in FIG. 5A. This device allows a standard guidewire (310) to be placed into the vessel, V, using a standard Seldinger approach. A guidewire (170) could range from 0.010 to −0.038 inches but it would be preferred to use the smaller diameter guidewire (170) to minimize the profile of the delivery catheter (10). After the standard guidewire (310) is in place across the arteriotomy site, AS, the delivery catheter (10) can be advanced over the standard guidewire (310) with cone (110) dilating the small diameter arteriotomy site, SAS, and the case (190) holding the small arteriotomy site, SAS, outwards. The delivery catheter (10) is advanced until the cone (110) comes into contact with the large diameter introducer sheath that is being used for passage of a large therapeutic device such as the TAVI or AAA catheters as shown in FIG. 5B. The large diameter introducer is removed and the delivery catheter (10) is positioned adjacent to the large diameter arteriotomy site, AS, and the stent device (20) is delivered in a manner that is similar to that described for the previous embodiment.

The present invention does not require that a balloon (60) (as shown in FIG. 1A) be used to deliver a self-expanding stent device (20). As seen in FIG. 6 a self-expanding stent device (20) can be positioned toward the distal end of a catheter shaft (320) having a cone (110) positioned at its distal end. The stent device (20) is contained by an external sheath or case (190) that can be withdrawn to release the stent device (20). A pusher tube (330) located on the catheter shaft (320) can be used to hold the stent device (20) in place along the catheter shaft (320) while the case (190) is being withdrawn. A control fiber (340) can form a loop (350) around one of the struts (200) of the stent (80) of the stent device (20) to hold the stent device (20) from embolizing or moving out of position within the blood vessel after it has been released. A secondary step could be implemented after the stent device (20) has been released and the catheter shaft (320) has been removed from the vessel. A standard balloon dilatation catheter can be introduced into the external sheath or case (190) to provide a post dilatation to the self-expanding stent device (20) to ensure that it is in full apposition with the vessel wall.

In another embodiment a stent (80) or stent device (20) can have a stent structure with a hinge (360) and strut (200) geometry as described in the cross referenced US patents and US patent application indicated earlier in this application. A balloon expandable hinge (360) and strut (200) structure is shown in FIGS. 7A and 7B. The hinge (360) is the portion of the stent (80) that undergoes deformation as the stent (80) is expanded from nondeployed state to a deployed expanded diameter state. The hinge (360) has a short hinge length (380) that undergoes all of the deformation as the hinge (360) is bent along the hinge length (380) during expansion deformation. The hinge length (380) for the balloon expandable stent is very short ranging from 1-3 times a hinge width. The hinge length (380) should be shorter than the hinge width to provide the maximum focus for hinge (360) deformation during the expansion deformation. The hinge length (380) is also smaller than the hinge radial dimension (400). The hinge radial dimension (400) extends in the radial direction of the stent (80) and is larger than the strut radial dimension (410) such that the hinge (360) will not bend if the stent (80) of the stent device (20) is placed into an oval cross section or crush deformation due to exposure to an external force or due to exposure imposed by neighboring muscle groups of the body. The strut radial dimension (410) is smaller than the hinge radial dimension (400) such that the strut (200) will flex easily to allow the stent (80) to form an oval shape during a crush deformation and will return elastically to its normal shape to provide the stent (80) with a round shape when the crush deformation force has been removed. The strut width (420) is larger than the hinge width such that during the expansion deformation, the strut (200) does not bend and instead forces all of the expansion deformation to occur at the hinges (360).

In FIG. 7A the hinge (360) is connected to two struts (200) via two transition regions (430). The transition regions (430) do not flex in either the expansion deformation or a crush deformation. The transition region radial dimension for this embodiment tapers from the strut radial dimension (410) to the hinge radial dimension (400). The cross sectional area (defined by the radial direction and width direction) of the transition region (430) is larger than that of the strut (200) or the hinge (360). The embodiment of FIG. 7B has two hinges (360) each of which connect to a strut (200) via a transition region (430). Each hinge (360) of this embodiment connect to the other hinge (360) via a node (440) that does not bend during the expansion deformation and does not bend in the radial direction during a crush deformation. The other reference numerals used in FIG. 7B represent similar components as found in FIG. 7A.

The use of a balloon expandable stent device (20) of the present embodiment either with or without a covering (100) allows the stent device (20) to be crimped onto the balloon (60) of the present invention as described in FIG. 1A-1C. Upon removal of the external sheath or case (190), the stent (80) will remain in position adjacent to the arteriotomy site and held onto the balloon via a crimping mechanism. Expansion of the balloon (60) will place the stent device (20) into direct apposition with the vessel wall such that the stent (80) or stent device (20) will generate hemostasis. If the femoral artery is exposed to external forces, the stent (80) will bend elastically along the struts (200) to an oval shape and will return to a round shape. The wall structure for the stent (80) of the stent device (20) of this embodiment can be an open structure, closed structure, a zigzag structure; it can have individual zigzag ringlets (225), or connectors (220) that join individual stent ringlets (225), or a spiral shaped zigzag structure; the stent (80) can be formed from a single ringlet (225) located and attached to each end of the covering (100), or it can extend throughout most or all of the covered stent device (20).

A self-expanding stent device (20) of still another embodiment provides a stent (80) that has a self-expanding hinge structure as shown in FIG. 8. The difference in this embodiment from that described in FIGS. 7A and 7B is that the hinge length (380) is longer. The expansion deformation of this embodiment is not focused as it was in the balloon expandable hinge geometry shown in FIGS. 7A and 7B. Instead the expansion deformation is spread along a hinge length (380) that extends from the junction of the hinge (360) from one transition region (430) to another transition region (430) as shown in FIG. 8. The hinge length (380) for the self-expanding stent device (20) is larger than 3 times the hinge width (390). The hinge length (380) for materials such as stainless steel or other generally plastically deformable metals is greater than twice the strut width (420). The long hinge length (380) allows the hinge (360) to undergo a deformation during compression for delivery within the external sheath in a smaller diameter state and undergo expansion deformation elastically to an enlarged expanded diameter upon release into the blood vessel. Thus the long hinge length (380) provides the stent device (20) with its self-expanding character. Other reference numerals describe similar components described in FIGS. 7A and 7B.

The self-expanding hinge stent (80) of FIG. 8 can be used in the stent device (20) of the present invention to provide a stent (80) that has very soft flex in a crush deformation by forming a strut (200) with a strut radial dimension (410) that is relatively small (i.e., 0.002-0.003 inches) in comparison to existing femoral stents, (i.e., 0.004-0.005 inches). The hinge radial dimension (400) can be relatively larger (i.e., 0.006 inches) than existing femoral stent (0.004-0.005 inches) to provide a stronger stent that resists reduction in diameter.

The balloon expandable hinge stent (80) of FIGS. 7A and 7B can be combined with any self-expanding stent including the self-expanding hinge stent (80) of FIG. 8 to form a stent having both a self-expanding portion (450) and a balloon expandable portion (460) as shown in FIGS. 9A and 9B. Balloon expandable ringlets (225) can be placed at each end of the stent device (20) such that the stent device (20) is firmly attached to the balloon (60) as shown in FIG. 9B; the central stent portion of the stent device (20) can be formed from self-expanding ringlets (225). The ringlets (225) can be attached directly to the covering (100) or can be attached to each other via connectors (220) or via one or more biodegradable fibers (480). Alternately, one or more balloon expandable ringlets (225) can be place in the central portion of the stent device (20) and one or more self-expanding ringlets (225) can be placed at the end portions of the stent device (20) as shown in FIG. 9A. The self-expanding ringlets (225) provide a soft and flexible deformation that is desirable in the femoral artery near the arteriotomy site.

In a further embodiment a locator balloon (490) is placed into the large introducer sheath, IS, prior to introduction of the delivery catheter (10) of the present invention to help position the delivery catheter (10) as shown in FIGS. 10A-10D. The locator balloon (490) is placed into the blood vessel, V, and inflated via a locator balloon inflation port (495) with an inflation medium that can include saline, air, CO2, contrast medium, or a cross-linkable polymer. The locator balloon (490) is pulled back to the arteriotomy site, AS, along with the large introducer sheath, IS. The locator balloon (490) provides hemostasis to the arteriotomy site and also can be used to occlude or partially occlude the vessel lumen, VL, as shown in FIG. 10B. As the delivery catheter (10) is introduced into the vessel lumen, VL, as shown in FIGS. 4A-4D, the delivery catheter (10) impinges upon the locator balloon (490), thereby stopping the delivery catheter (10) from further advancement past the locator balloon (490).

A tether fiber (500) of one embodiment is attached to the distal end (510) of the locator balloon (490). Applying tenstion to the tether fiber (500) via a tensioning spool (515) will cause the locator balloon (490) to form inward folds (520) and advance inside of the locator balloon shaft (525) thereby providing a passage for the delivery catheter (10) at a location adjacent to the arteriotomy site, AS, as shown in FIG. 10C. The locator balloon (490) still provides hemostasis of blood at the arteriotomy site. The stent device (20) of the delivery catheter (10) is then released adjacent to the arteriotomy site, AS, and into contact with the locator balloon (490). The locator balloon (490) can fully withdrawn into the locator balloon (490) shaft and out of the arteriotomy site, AS, as the balloon (60) from the delivery catheter (10) is delivered into apposition with the vessel wall at the arteriotomy site as shown in FIG. 10D. The locator balloon (490) can be formed with more than one tether or with a shape that enhances its ability to provide positioning for the delivery catheter (10) and also to provide hemostasis for the arteriotomy site.

Figure 11B:
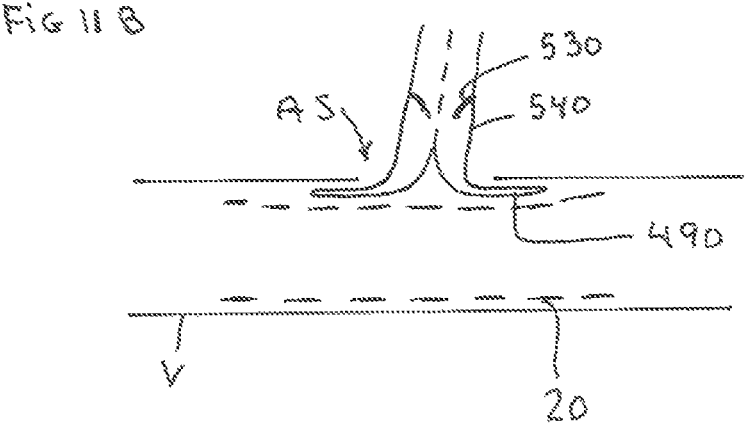
FIG. 11B is a plan view of an implantable locator balloon located within the arteriotomy site and having a stent device placed into apposition with the locator balloon to generate hemostasis.

The locator balloon (490) can alternately be partially implanted and serve as a plug for the arteriotomy site as shown in FIGS. 11A and 11B. In FIG. 11A the locator balloon (490) has been filled with a cross-linking polymer such as polyurethane, silicone, or a biodegradable material such as polyethylene glycol, or other biodegradable gel or fluid including saline. A balloon valve (530) is located near the junction of the locator balloon (490) with the locator balloon (490) distal shaft such that the inflation fluid can enter but cannot leak out of the locator balloon (490) and through the locator balloon shaft (525). A temporary passage (not shown) can be provided to allow inflation fluid to leak out of the locator balloon (490) and through a temporarily placed passage tube that extends through the balloon valve (530), for example. As the stent device (20) is dilated via the delivery catheter (10) to provide apposition of the stent device (20) with the vessel wall, the inflation fluid within the locator balloon (490) is forced to push the locator balloon (490) into forming a seal with the arteriotomy site. The locator balloon proximal shaft (550) is separated from the locator balloon distal shaft (540) via a threaded uncoupling or any other uncoupling mechanism that can be used to uncouple two tubings with a common lumen. The balloon valve (530) remains implanted in the arteriotomy site along with the locator balloon (490). The stent device (20) in this embodiment could include the stent (80) either with or alone without a covering (100) and depend upon the locator balloon (490) to provide the seal for the arteriotomy site.

The material of construction for the locator balloon (490) include nylon, pebax, polyethylene terephthalate (PET), polyurethane, silicone, or other compliant, semicompliant, or noncompliant materials used for balloon, stent (80), or implanted medical device manufacture in the medical device industry. The locator balloon (490) can also be formed from thin-walled ePTFE, a thin tissue material, or a flexible biodegradable tissue or film. The tether fiber (500) can be formed from a thin metal or polymeric fiber and can also be formed from a biodegradable material. The locator balloon distal shaft (540) can be formed from a polymeric material including a biodegradable materials indicated for the locator balloon (490). The tether valve can be a standard duck-billed valve formed from a thin polymeric leaflets or tissue leaflets; the tether valve can also be formed from biodegradable materials indicated for the locator balloon (490).

The dimensions for the locator balloon (490) as it is being used is further described during the following method steps. The locator balloon (490) is folded during entry into the large introducer sheath, IS, and into the vessel lumen, VL, of the blood vessel, V. The locator balloon (490) is then inflated via the locator balloon inflation port (495) with inflation medium to a volume or pressure that causes it to expand to a diameter that is 10-50% larger than the arteriotomy site, AS, and the inside diameter of the IS; this diameter can range from 4-11 mm; the locator balloon inflated diameter is approximately 6-9 mm for a TAVI procedure access site arteriotomy. The locator balloon shaft (525) is withdrawn proximally until the locator balloon (490) is in full contact with the arteriotomy site and the IS has its distal end adjacent the locator balloon (490). The locator balloon (490) is then inflated to a diameter that fills the lumen of the femoral artery, approximately 7-10 mm to provide an inflated locator balloon (490) into which the delivery catheter (10) will contact when it is inserted. The locator balloon (490) can have traction applied to the tether fiber (500) to cause the distal end of the locator balloon (490) to inwardly fold into the locator balloon shaft (525) and provide a space in the lumen of the blood vessel, V, for passage of the delivery catheter (10).

The embodiments of the present invention include both self-expanding and balloon expandable stents and covered stents (90) that form the stent device (20). The stents (80) can be formed from single ringlets (225) located at the end of the covering (100) or can extend throughout the stent device (20). The delivery catheter (10) and stent device (20) can be used with a balloon dilatation catheter or without, and can be used with or without the locator balloon (490). Each of the embodiments can be interchanged with other aspect of other embodiments and still are included in the present invention.

The invention claimed is:

1. A catheter assembly that provides percutaneous access through a wall of a blood vessel of the body and provides delivery of an implanted device into a neighboring portion of the same blood vessel of the body, said catheter assembly comprising, A. a shaft having a nondeformable cone located at its distal end, and a balloon permanently affixed in position relative to said cone, said cone configured to make direct contact with the vessel wall and having a taper configured to dilate and advance said cone through the vessel wall during cone advancement into the blood vessel, B. a stent device mounted on said balloon adjacent said cone, said stent device comprising self-expanding elements, C. a movable sheath that is positioned on an outside of said stent device, a distal end of said sheath making smooth contact with a surface of said cone during advancement of said cone through the vessel wall, said stent device being held b said sheath into a small diameter configuration during delivery of said catheter assembly into the blood vessel, D. a guidewire having a free distal end and a proximal end said free proximal end having a guidewire attachment element affixed thereto, E. said cone having a cone attachment element located at its distal end, said cone attachment element providing attachment to said guidewire attachment element to form a fixed joint between said cone and said guidewire following placement of said guidewire into the blood vessel.

2. The catheter assembly of claim 1 further comprising a wrap attachment on said balloon, said wrap attachment joining stent struts of said stent device to said balloon, said wrap attachment being released upon expansion of said balloon.

3. The catheter assembly of claim 1 wherein said stent device further comprises a thin covering attached to a surface of said stent.

4. The catheter assembly of claim 3 wherein said thin covering is expanded polytetrafluoroethylene material.

5. The catheter assembly of claim 1 wherein said stent has struts that are overlapped with other struts in a circumferential direction to provide a low profile for the stent and provide a large expansion ratio.

6. The catheter assembly of claim 1 wherein said stent has struts that are overlapped with other struts in an axial direction to provide a low profile for the stent and provide a large expansion ratio.

7. The catheter assembly of claim 1 wherein said stent device comprises a balloon expandable hinge stent portion, said hinge stent portion comprised of at least one hinge and at least one strut having a hinge radial dimension that is greater than a strut radial dimension of the at least one strut and a hinge length that is shorter than a hinge width.

8. The catheter assembly of claim 7 wherein said stent device has a self-expanding portion, said self-expanding portion comprised of at least one hinge and at least one strut having a hinge radial dimension that is greater than a strut radial dimension b5of the at least one strut and a hinge length that is greater than three times the hinge width.

9. The catheter assembly of claim 1 further comprising a guidewire tubing extending through said shaft and, said guidewire tubing providing passage for an interventional device through said shaft.

10. The catheter assembly of claim 1 b6wherein said free proximal end of the guidewire is joined permanently to a distal end of said cone.

11. The catheter assembly of claim 1 further comprising a locator balloon joined to a distal end of a locator balloon shaft, said locator balloon being deliverable through a therapeutic introducer sheath and inflatable to a significantly larger diameter than the introducer sheath; said locator balloon having a tether fiber attached at a distal end of said locator balloon, said tether fiber extending through an inside of said locator balloon and into said locator balloon shaft, said locator balloon providing contact with said cone for stent device positioning.

12. The catheter assembly of claim 11 wherein said locator balloon further comprises a tensioning spool to apply tension to said tether fiber thereby advancing said locator balloon into said locator balloon shaft and forming inward folds in said locator balloon.

13. A catheter assembly for percutaneous access into a vessel of the body, said catheter assembly comprising, A. a balloon tube having a balloon located at its distal end, B. a stent device mounted on an outside of said balloon, said stent device comprising a stent having a covering attached thereto, C. said stent being comprised of hinges and struts, each of said hinges having a hinge radial dimension that is larger than a strut radial dimension of each of said struts, each of said hinges having a hinge length that is larger than a hinge width to focus the deformation of each of said hinges, D. a nondeformable cone attached to a distal end of said balloon, said cone having a taper that is configured to make direct contact with an arteriotomy in the vessel to open the arteriotomy outwards during advancement of the cone into the vessel, E. a movable sheath that is positioned on an outside of said stent device, said sheath being in direct contact with said cone and configured to be in direct contact with the arteriotomy to hold it outward, F. a guidewire having a free distal end and a free proximal end, said free proximal end having a guidewire attachment element affixed thereto, said cone having a cone attachment element located at its distal end, said cone attachment element providing attachment to said guidewire attachment element to form a fixed joint between said, cone and said guidewire following placement of said guidewire into the vessel.

14. The catheter assembly of claim 13 wherein said stent further comprises a self-expanding portion.

15. The method of use of a catheter assembly in a vessel of the body comprising the steps, A. providing the catheter assembly of claim 1, B. advancing the guidewire across the wall of the vessel, C. attaching the free proximal end of said guidewire to a distal end of the cone, D. advancing said catheter and guidewire into a lumen of the vessel, E. withdrawing said movable sheath, F. expanding said balloon to force said stent device into contact with the wall of the vessel.

16. The method of claim 15 wherein said stent device further comprises a thin covering attached to a surface of said stent device.

17. The method of claim 15 wherein said stent device comprises a balloon expandable stent having at least one hinge and at least one strut, said hinge having a hinge radial dimension that is larger than a strut radial dimension, said hinge having a hinge length that is smaller than a hinge width.

18. A catheter assembly that provides percutaneous access through a wall of a blood vessel of the body and provides delivery of an implanted device into the blood vessel of the body, said catheter assembly comprising, A. a shaft having a nondeformable cone located at its distal end, said cone formed from a nondeformable material that is configured to make direct contact with a vessel wall and having a taper to dilate and advance said cone through the vessel wall during cone advancement into the vessel, B. a stent device mounted on said shaft adjacent said cone, C. a movable sheath that is positioned on an outside of said stent device, a distal end of said sheath being in direct contact with said cone, said sheath making smooth contact with a surface of said cone, said stent device being contained within said sheath in a small diameter configuration during delivery of said catheter assembly into the blood vessel, D. a guidewire having a free distal end and a free proximal end, said free proximal end having a guidewire attachment element affixed thereto, E. said cone having a cone attachment element located at its distal end, said cone attachment element providing attachment to said guidewire attachment element to form a fixed joint between said cone and said guidewire following placement of said guidewire into the blood vessel.

* * * * *